US00PP10334P

United States Patent [19]

Carruth

[11] Patent Number: Plant 10,334

[45] Date of Patent: Apr. 21, 1998

[54] FLORIBUNDA ROSE PLANT NAMED 'WEKCALROC'

[75] Inventor: Thomas F. Carruth, Altadena, Calif.

[73] Assignee: Weeks Wholesale Rose Grower, Inc., Upland, Calif.

[21] Appl. No.: 816,868

[22] Filed: Mar. 13, 1997

[51] Int. Cl.[6] ..... A01H 5/00

[52] U.S. Cl. ..... Plt./22

[58] Field of Search ..... Plt./7.1, 22, 11, Plt./12, 13, 1

*Primary Examiner*—Howard J. Locker

*Attorney, Agent, or Firm*—Christie, Parker & Hale, LLP

[57] ABSTRACT

A new variety of Floribunda rose suitable for garden decoration, having flowers of striped red and yellow coloration.

1 Drawing Sheet

BACKGROUND OF THE INVENTION

This invention relates to a new and distinct variety of Floribunda Rose. The varietal denomination of the new variety is 'Wekcalroc'. It has as its seed parent the variety known as 'Calico' (U.S. Plant Pat. No. (4,006) and as its pollen parent the variety known as 'Macminmo' (U.S. Plant Pat. No. (7,319).

SUMMARY OF THE INVENTION

Among the features which distinguish the new variety from other presently available and known commercial rose cultivars are the following combination of characteristics: its unusual irregularly striped coloration of red and yellow on the upper petal surface and solid yellow coloration on the under petal surface, its very darkly pigmented young foliage, its growth with numerous prickles of varying sizes, and its combination of fruity and citrus-like fragrances. The plant is a bushy compact plant suitable for outdoor garden decoration. 'Wekcalroc' may be asexually propagated by cuttings, budding, or grafting.

Asexual reproduction of the new variety by budding as performed in Kern County, Calif. and Upland, Calif. shows that the foregoing and other distinguishing characteristics come true to form and are established and transmitted through succeeding propagations.

COMPARISON WITH PARENTS

The new rose may be distinguished from its seed parent, 'Calico' by the following combination of characteristics: whereas 'Calico' is classified as a Hybrid Tea, 'Wekcalroc' is classified as a Floribunda. The new rose bears medium sized flowers of a striped yellow and red coloration, whereas the seed parent bears significantly larger flowers of a blended yellow and pink coloration. 'Wekcalroc' bears flowers with a sweet fragrance and 'Calico' bears flowers with only a very light fragrance.

The new variety may be distinguished from its pollen parent, 'Macminmo' by the following combination of characteristics: whereas 'Wekcalroc' bears medium-sized flowers of a striped red and yellow coloration, 'Macminmo' bears significantly smaller flowers with a striped red and white coloration. The flowers of the pollen parent are semi-double in petalage (about 6 to 14 petals), whereas the new variety bears flowers with significantly higher petalage (about 29 to 35 petals). 'Macminmo' has small foliage and a spreading habit, whereas 'Wekcalroc' has significantly larger foliage and a more bushy compact mature habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of this character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotypic expression may vary with environmental, cultural and climatic conditions, as well as differences in conditions of light and soil.

FLOWER

The new variety bears its flowers sometimes singly, usually in clusters of three to five or more per stem. Flowers are borne in irregular somewhat flat clusters on strong short to medium length stems (about 15 to about 22 cms.). Outdoors, the plant blooms abundantly and nearly continuously during the growing season. The flowers have a moderate fruity to citrus-like fragrance.

BUD

The peduncle is about 5 to about 6.5 cms. in length, of average to heavy caliper, and usually stiff. It is moderately rough, with many stipitate glands and some very small prickles; prickle color is near 183D. Peduncle color is between 137B and 144A sometimes moderately suffused with between 176A and 176B on the side facing the sun.

Before the calyx breaks, the bud is about 1.6 to about 2 cms. in diameter at the widest point, about 1.8 to about 2.3 cms. in length, and pointed to ovoid to nearly globular in shape. The surface of the bud bears some stipitate glands, usually with slender entire foliaceous parts extending beyond the tip of the bud equal to ¼ or more of its length. Bud color is between 137B and 144A sometimes moderately suffused with between 176A and 176B on the side facing the sun.

The inner surface of the sepals is covered with fine wooly tomentum; sepal margins are lined with many stipitate glands.

As the petals open, the bud is about 2.2 to about 2.8 cms. in diameter at the widest point, about 2.5 to about 3 cms. in length, and somewhat flat-topped to globular in form. The color of the under surfaces of the newly opened petals is between 14C and 12B at the petal base fading to between 10D and 12C toward the top of the petal. Sometimes the area exposed to the sun is irregularly striped and blushed with as dark as between 53A and 46A to as light as between 54B and 55C.

The color of the upper surfaces of the newly opened petals is irregularly striped and flecked with as dark as between 46A and 53A or as light as between 12C and 18A. At the point where the petal attaches, there is a medium to large zone of between 15C and 12B.

BLOOM

When fully open, the bloom is medium size to large for the class, ranging from about 8 to about 10 cms. in diameter. Petalage is double with about 29 to 35 petals and about 3 to 5 petaloids arranged irregularly. When partially open, the bloom form is somewhat flat-topped to ruffled, and the petals are moderately spiraled to undulated with petal edges slightly reflexed outward. When fully open, the bloom form is less flat to more ruffled and somewhat globular, and the petals are somewhat more cupped to undulated with petal edges only slightly reflexed outward.

PETALS

The substance of the petals is moderately heavy and of medium thickness, with upper surfaces somewhat velvety to satiny and under surfaces slightly shiny. The outer petals are nearly round to broadly obovate in shape with rounded apices. The inner petals are more narrowly obovate in shape with rounded apices.

NEWLY OPENED FLOWER

The under surface of the outer, intermediate and inner petals is between 14C and 12B at the petal base fading to between 10D and 12C toward the top of the petal.

The upper surface of the outer petals is irregularly striped and flecked with as dark as between 46A and 53A to as light as between 12C and 18A. The yellow pigmented areas near the petal edge that are exposed to the sun sometimes blush to between 55B and 55C. At the point where the petal attaches, there is a medium to large zone of between 15D and 12B.

The upper surface of the intermediate and inner petals is irregularly striped and flecked with as dark as between 46A and 53A to as light as between 12C and 18A with no blush coloration. At the point where the petal attaches, there is a medium to large zone of between 15D and 12B.

The general tonality of the newly opened flower is irregularly striped and flecked with as dark as between 46A and 53A to as light as between 12C and 18A.

THREE DAY OLD FLOWER

The under surface of the outer and inner petals is between 10C and 12C at the petal base fading to between 10D and 11D toward the top of the petal.

The upper surface of the outer and inner petals is irregularly striped and flecked with as dark as between 46A and 53B to as light as between 18C and 11C. The yellow pigmented areas near the petal edge that are exposed to the sun sometimes blush to between 55D and 55C. At the point where the petal attaches, there is a medium to large zone of between 11B and 12C.

The general tonality of the three day old flower is irregularly striped and flecked with as dark as between 46A and 53B to as light as between 18C and 11C. The yellow pigmented areas near the petal edge that are exposed to the sun sometimes blush to between 55D and 55C.

On the spent bloom, the petals usually drop off cleanly.

In September, blooms on the bush growing outdoors generally last from three to four or more days. Cut roses grown outdoors and kept at normal indoor living temperatures generally last from three to four days.

MALE REPRODUCTIVE ORGANS

Stamens are average in number and are arranged regularly about the pistil. The filaments are of medium in length, most with anthers. The anthers are moderately small for the class and all open approximately at the same various time. Anther color is near 17C when immature and near 165A at maturity. Pollen is somewhat sparse and near 16C in color.

FEMALE REPRODUCTIVE ORGANS

Pistils vary in number (approximately 55). The styles are somewhat uneven, average in length and in caliper, and somewhat loosely bunched. Stigma and style color is near 5C. Ovaries are usually all enclosed in the calyx.

Hips have not been observed on this variety when grown in Upland, Calif.

FOLIAGE

The compound leaves are usually comprised of three to five or more leaflets and are borne abundantly. The leaves are about 9 to about 11.5 cms. in length, about 7.5 to about 9.5 cms. in width at the widest point, somewhat heavy in texture, and semi-glossy to matte in finish. The leaflets are about 3.5 to about 6.5 cms. in length, about 2.5 to about 3.5 cms. in width at the widest point, very oval in shape with acute apices and bases. Their margins are usually simply serrate.

The upper and under surface of the mature leaf is between 137A and 147A. The under surface of the mature leaf is between 138A and 148B, sometimes irregularly lightly suffused with near 183C. The upper and under surface of the young leaf is between 137C and 147B, often heavily suffused with between 187A and 183A. The under surface of the young leaf is near 148B, often heavily suffused with near 183A.

The rachis is somewhat light to average in caliper and moderately smooth. The upper side is moderately grooved with few hairs and stipitate glands on the edges of the grooves. The under side of the rachis is predominantly smooth with few small prickles.

The stipules are medium to somewhat long in length with somewhat narrow moderately long straight points that usually turn out at an angle of more than 45 degrees.

The plant displays an above average degree of resistance to powdery mildew and blackspot and rust as compared to other commercial varieties grown under comparable conditions in Upland, Calif.

GROWTH

The plant has a bushy compact upright low to medium height habit (about 90 to about 130 cms. in height and about 70 to about 100 cms. spread at the widest point), with full branching. It displays very vigorous growth and the canes are of moderate heavy caliper.

The color of the major stems is between 146B and 148A. They bear numerous prickles of varying sizes ranging from about 0.4 to about 1.3 cms. in length. The prickles are almost straight, angled slightly downward, with a moderately short length, somewhat broad base; prickle color is between 166C and 164A.

The color of the branches is between 146A and 137B. They bear numerous prickles which are of similar size and shape to the prickles on the major stems; prickle color is between 160B and 162C.

The color of the new shoots is near 144A often heavily suffused with between 187B and 183B. They bear numerous prickles which are of similar shape to the prickles on the major stems; length of the immature prickles is about 0.2 to about 0.7 cms. Prickle color is near 187C.

I claim:

1. A new and distinct variety of Floribunda rose plant substantially as described and illustrated herein.

* * * * *

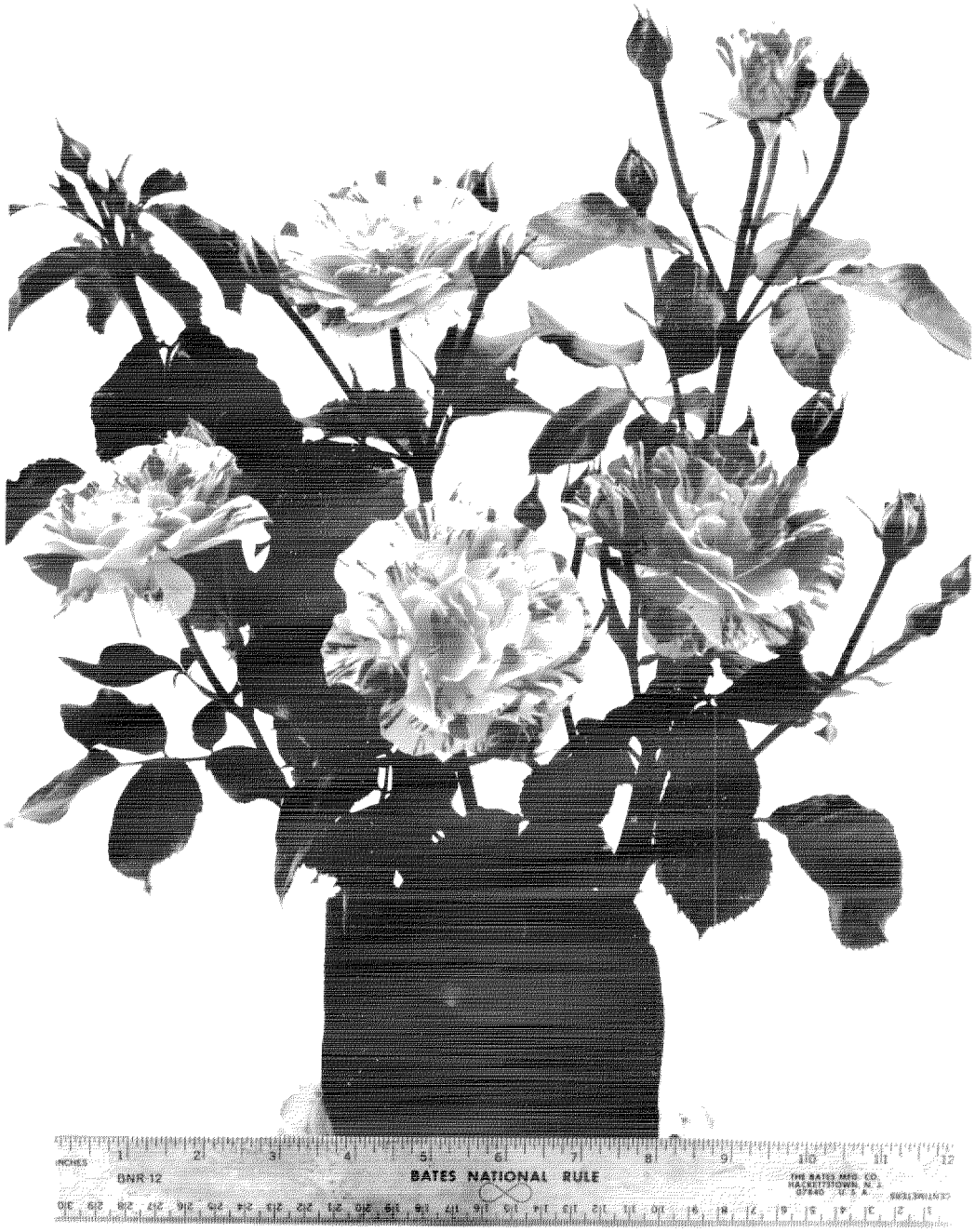
BNR 12
BATES NATIONAL RULE